US008552860B2

(12) United States Patent
Baughman et al.

(10) Patent No.: US 8,552,860 B2
(45) Date of Patent: Oct. 8, 2013

(54) BINAURAL AUDIO SIGNAL-BASED APPLICATIONS

(75) Inventors: Aaron K. Baughman, Silver Spring, MD (US); Christian Eggenberger-Wang, St. Gallen (CH); Peter K. Malkin, Ardsley, NY (US)

(73) Assignee: International Business Machines Corporation, Armonk, NY (US)

( * ) Notice: Subject to any disclaimer, the term of this patent is extended or adjusted under 35 U.S.C. 154(b) by 426 days.

(21) Appl. No.: 12/943,655

(22) Filed: Nov. 10, 2010

(65) Prior Publication Data

US 2012/0112909 A1    May 10, 2012

(51) Int. Cl.
*G08B 21/00* (2006.01)
(52) U.S. Cl.
USPC .......................................... 340/540; 600/545
(58) Field of Classification Search
USPC ............................. 340/540; 600/544, 545, 559
See application file for complete search history.

(56) References Cited

U.S. PATENT DOCUMENTS

| 5,213,562 | A | 5/1993 | Monroe | |
|---|---|---|---|---|
| RE36,348 | E | 10/1999 | Carter et al. | |
| 6,456,199 | B1 * | 9/2002 | Michael | 340/540 |
| 7,769,439 | B2 * | 8/2010 | Vesely et al. | 600/544 |
| 2006/0116600 | A1 | 6/2006 | Vesely et al. | |
| 2007/0282216 | A1 * | 12/2007 | Vesely et al. | 600/545 |

FOREIGN PATENT DOCUMENTS

| WO | 2008131454 A1 | 10/2008 |
|---|---|---|
| WO | 2009054699 A1 | 4/2009 |

OTHER PUBLICATIONS

Settapat, S., et .al., "An alpha-activity-based binaural beat sound entrainment system using arousal state model", Proceedings of the 2008 International Conference on Advances in Computer Entertainment Technology, ACE 2008, p. 63-66, 2008, ACM.
Wahbeh et al., "Binaural Beat Technology in Humans: A Pilot Study to Assess Psychologic and Physiologic Effects", The Journal of Alternative and Complementary Medicine, vol. 13, No. 1, 2007, pp. 25-32.
Lewis et al., "The Effect of Hemispheric Synchronization on Intraoperative Analgesia", International Anesthesia Research Society, Anesth Analg 2004;98, Sep. 2, 2003, pp. 533-536.
Padmanabhan et al., prospective, randomised, controlled study examining binaural beat audio and pre-operative anxiety in patients undergoing general anaesthesia for day case surgery, Anaesthesia, 2005, 60, pp. 874-877.
Sharp et al., "Screening for Depression Across the Lifespan: A Review of Measures for Use in Primary Care Settings", http://www.aafp.org/afp/2002/0915/p1001.htm, AmFam Physician, Sep. 2002, pp. 1001-1009.

* cited by examiner

*Primary Examiner* — John A Tweel, Jr.
(74) *Attorney, Agent, or Firm* — Douglas A. Lashmit; Hoffman Warnick LLC (57) ABSTRACT

Applications for detecting binaural sounds and customizing binaural sounds for users. A system is disclosed having: an interface for obtaining a plurality of desired responses; a system for generating a binaural recipe, wherein the binaural recipe includes left side audio signals and right side audio signals for inducing the plurality of responses; and an output system for playing the left side audio signals and right side audio signals. A further system is disclosed for detecting binaural sounds, including: an input system for obtaining a left side audio signal and a right side audio signal within an environment; a binaural sound detector for evaluating the left side audio signal and the right side audio signal to determine whether a binaural sound is present; and an alarm system for generating an alert when the binaural sound is detected.

9 Claims, 5 Drawing Sheets

Figure 1

User Interface 34

Output Type:

- ☐ Rock Music
- ■ Jazz
- ☐ Classical
- ☐ Rap
- ☐ Broadway/Show
- ☐ Book
- ☐ News Desired Response(s):

- ☐ High Perception
- ■ Problem Solving
- ☐ Fear
- ☐ Active
- ☐ Busy
- ☐ Anxious
- ☐ Concentration
- ☐ Aroused
- ■ Cognitive
- ☐ Relaxed
- ☐ Pre-sleep
- ☐ Pre-awake
- ☐ Dream

- ☐ Happy
- ■ Calm
- ☐ Euphoric
- ☐ Sad
- ☐ Emotional

Figure 3

User Interface 34

Output Type:

- ☐ Rock Music
- ■ Jazz
- ☐ Classical
- ☐ Rap
- ☐ Broadway/Show
- ☐ Book
- ☐ News Binaural recipe:

- ☐ Formula 1
- ■ Formula 2
- ☐ Formula 3
- ☐ Formula 4
- ☐ Formula 5
- ☐ Formula 6
- ☐ Formula 7
- ☐ Formula 8
- ■ Formula 9
- ☐ Formula 10

User comments: 60

*Peaceful and tired*

BINAURAL AUDIO SIGNAL-BASED APPLICATIONS

BACKGROUND

The present invention relates to applications involving binaural sounds, and more particularly to, among other things, detecting binaural signals, blocking binaural signals and customizing binaural signals for a specific individual.

Binaural sound provides a somatic and cognitive method to affect an individual while providing an effect on the environment. A sound is composed of simultaneous waves of a given frequency and amplitude. The summation of all sound waves at a given time produces music or noise. When two sound waves are separated by close to 30 hertz, a binaural sound (also referred to as binaural beats) is produced. Much like visual 3D, the resulting sound is an acoustic 3D source. For example, the right ear will receive a sound of X hertz while the left ear receives a sound of X+30 hertz. The frequency difference between the two sounds invokes potential differences within the human brain causing changes in mood, psychiatric conditions, etc.

The use of binaural sound has been proposed for numerous applications. For example, binaural sound can be used to reduce the amount of anesthesia required during surgery since binaural sound can invoke brain waves that cause sedation or analgesia; binaural sound can reduce anxiety within patients, a bank and combination of binaural sound can help reduce obsession compulsive disorder, reduce the need for drugs and optimize human moods. Sales organizations can utilize the sounds to associate a pleasant feeling with a product, a natural extension of pleasant aromas and music.

BRIEF SUMMARY

In a first aspect, a system for detecting binaural sounds is provided, comprising: an input system for obtaining a left side audio signal and a right side audio signal within an environment; a binaural sound detector for evaluating the left side audio signal and the right side audio signal to determine whether a binaural sound is present; and an alarm system for generating an alert when the binaural sound is detected.

In a second aspect, a binaural sound system is provided, comprising: an interface for obtaining a plurality of desired responses; a system for generating a binaural recipe, wherein the binaural recipe includes left side audio signals and right side audio signals for inducing the of plurality responses; and an output system for playing the left side audio signals and right side audio signals.

In a third aspect, a computer readable medium having a program product stored thereon for processing binaural sounds is provided, comprising: program code for obtaining a plurality of desired responses; program code for generating a binaural recipe, wherein the binaural recipe includes left side audio signals and right side audio signals for inducing the plurality of responses; and program code for outputting the left side audio signals and right side audio signals.

In a fourth aspect, a method for simulating a brain wave response within a user is provided, comprising: having a user engage in an experience; monitoring and recording brain wave changes in the user with a monitoring device; calculating a recipe for a binaural sound to recreate the brain wave changes; and producing an output to implement the recipe.

BRIEF DESCRIPTION OF THE SEVERAL VIEWS OF THE DRAWINGS

These and other features of this invention will be more readily understood from the following detailed description of the various aspects of the invention taken in conjunction with the accompanying drawings.

The drawings are merely schematic representations, not intended to portray specific parameters of the invention. The drawings are intended to depict only typical embodiments of the invention, and therefore should not be considered as limiting the scope of the invention. In the drawings, like reference numbering represents like elements.

DETAILED DESCRIPTION

Figure 1:
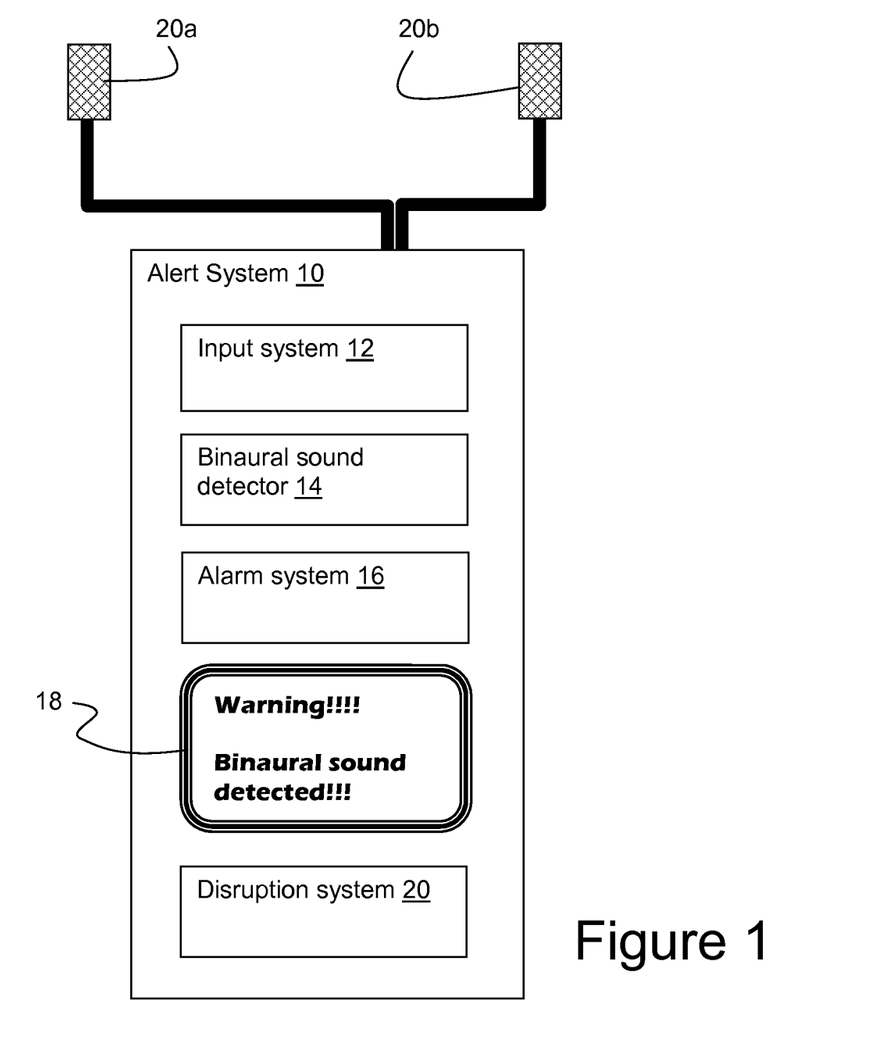
FIG. 1 depicts an alert system for detecting binaural sounds in accordance with an embodiment of the present invention.

Described are various embodiments that exploit the phenomena of binaural sounds. The embodiments may be integrated into a single device or system, or one or more aspects of the described embodiments may be implemented as independently. FIG. 1 depicts a first embodiment that provides an alert system 10 for detecting and alerting a user that binaural sounds are being utilized within an environment. For instance, a user listening to programming content via a set of headphones may be unknowingly targeted with a binaural sound to induce a desired reaction. Alert system 10 can be integrated into a device, such as a portable music player, portable satellite radio, automobile dashboard, stereo system, etc., or be implemented as a stand alone product. Alert system 10 generally includes: (1) a input system 12 for obtaining separate right-side and left-side audio signals; (2) a binaural sound detector 14 that analyzes the right-side and left-side audio signals to determine if a binaural signal exists; and (3) an alarm system 16 that outputs an alarm output 18 if binaural sound is detected. Alert system 10 may also include a disruption system 20 to disrupt the binaural sound.

Right-side and left-side audio signals may be obtained in any fashion, e.g., from microphones 20a, 20b, from a stream of digital data, from an analog transmission, etc. Once the signals are obtained, binaural sound is identified if there are signals between a specified frequency range being supplied to each side, e.g., 1000 and 1500 hertz (Hz), and if the signals differ in frequency, e.g., by less than 30 Hz. Any known techniques may be utilized to evaluate the signals and such techniques are well known in the art, e.g., the use of digital and/or analog filters, digital signal processing techniques, Fourier transforms, etc. Output 18 may comprise any device or system for outputting an alarm to the user, including audible output, e.g., broadcast over the content being listed to by the user, a visual output such as a display screen or graphical user interface, a vibration, an electronic notification such as an email or text message, etc.

In a further embodiment, a disruption system 20 may be implemented to disrupt a detected binaural sound. For instance, disruption system 20 may eliminate or alter one or both of the inputted left-side and right-side signals using known digital signal processing techniques such that, e.g., the signals do not differ by less than 30 Hz.

Figure 2:
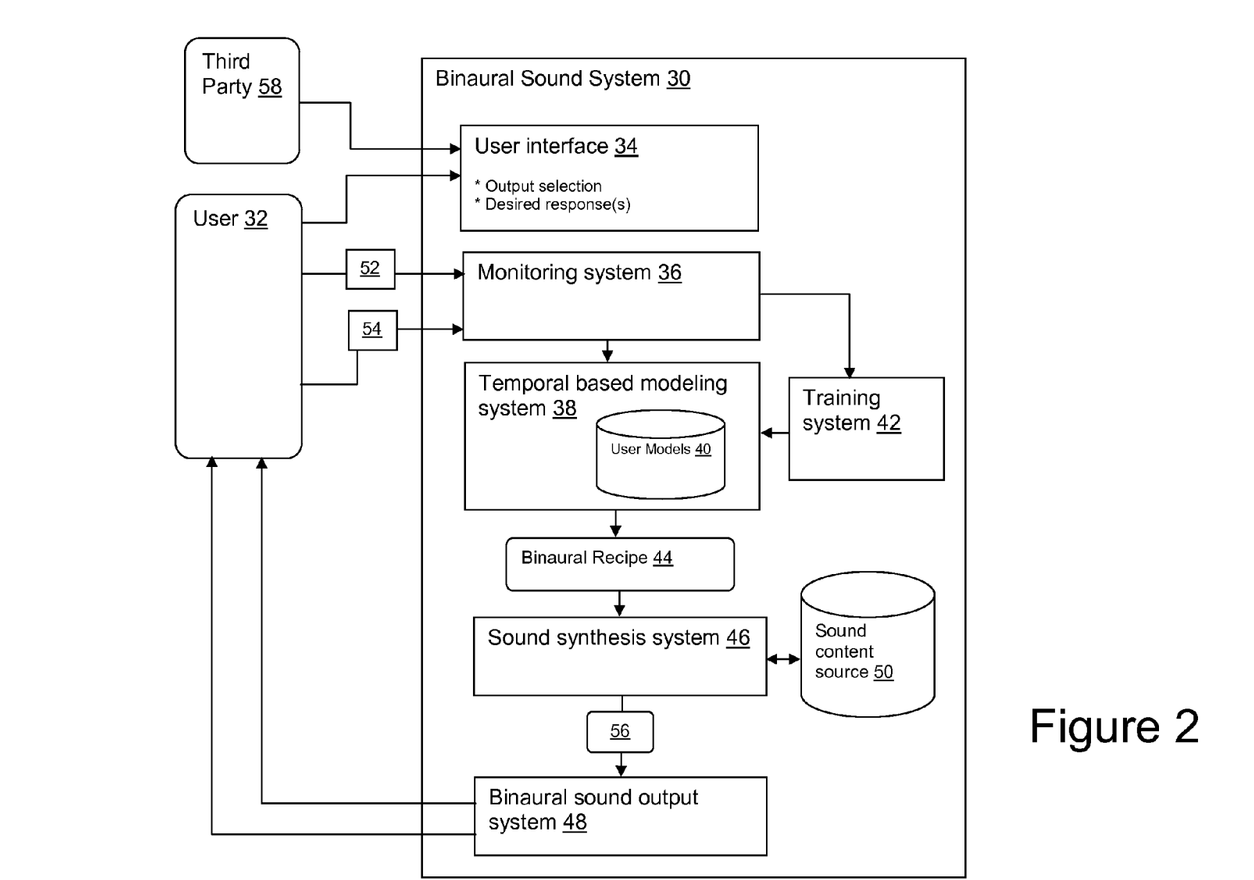
FIG. 2 depicts a binaural sound system in accordance with an embodiment of the present invention.

FIG. 2 depicts a binaural sound system 30 for allowing a user 32 to obtain a desired brain wave response using binaural sounds. Binaural sound system 30 generally includes: (1) a user interface 34 for allowing the user 32 or a third party 58 to, e.g., select a type of output such as a music genre, and one or more desired response states, e.g., relaxation, active concentration, problem solving, happiness, etc.; (2) a monitoring system 36 for monitoring a set of user conditions including, e.g., physiological, cognitive, behavioral and environmental inputs; (3) a temporal based modeling system 38 for implementing time based user models 40 to determine a binaural recipe 44 to achieve a set of desired responses based on the set of user conditions; (4) a sound synthesis system 46 for synthesizing a binaural sound from a sound content source 50; (5) a binaural sound output system 48 for generating and outputting the binaural sound back to the user 32; and (6) a training system 42 for training the user models 40. As can be seen, a feedback loop between the user 32 and binaural sound system 30 is established to allow for automated and/or manual adjustments in the binaural sounds to achieve the desired response for the user 32.

Figure 3:
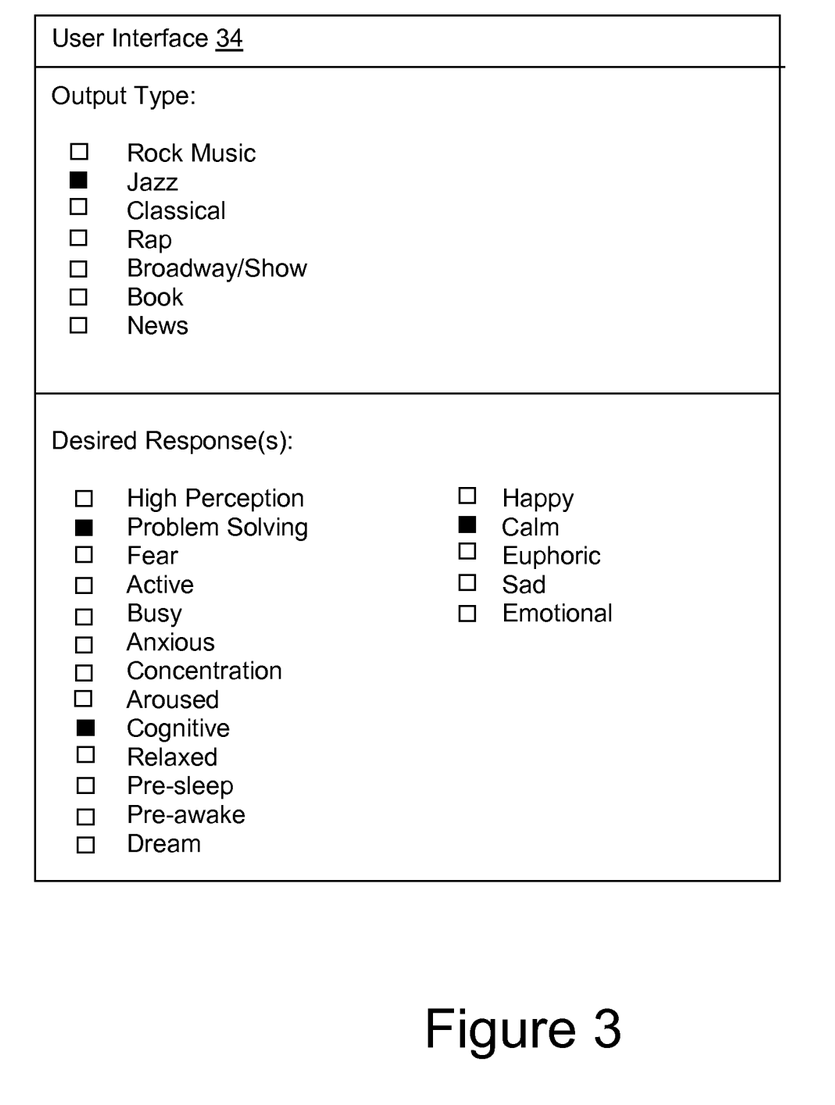
FIG. 3 depicts an illustrative interface for a binaural sound system in accordance with an embodiment of the present invention.

FIG. 3 depicts an illustrative example of a user interface 34 for allowing a user 32 (or third party 58) to manage the binaural sound generation process. In this example, the user 32 can select an output type, such as a music genre, book, news, etc., as well as one or more desired responses. For instance, if the user 32 was taking an exam, the user 32 might select: problem solving, cognitive and calm, as shown. Note that the user interface 34 allows the user 32 to select more than one desired response. Obviously, the specific implementation of the user interface 34 can vary and FIG. 3 is shown as one possible example. In another example, a third party 58, e.g., a host, an advertiser, an airline, etc., could select a set of desired responses.

Once the user 32 has inputted the desired response or responses via user interface 34, binaural sound system 30 can begin generating the appropriate binaural sound to the user 32. In order to facilitate this process, monitoring system 36 (FIG. 2) may be utilized to obtain current user conditions 52, including, e.g., a heart rate, blood pressure, user temperature, user movements such as foot tapping, room temperature, amount of light in the environment, retinal activity, user reflexes, breathing rates, time of day, etc. Any set of devices or systems for obtaining these conditions may be utilized, e.g., monitors, sensors, thermostats, motion detectors, etc.

Monitoring system 36 may also monitor a current response state 54 of the user 32, e.g., active, happy, euphoric, sad, etc., based on either manual inputs from the user 32 or from detected brain waves of the user 32. In one embodiment, the current response state 54 (e.g., increased theta waves) obtained during an act (e.g., closing eyes and meditating) or event (e.g., getting married) can be recorded by training system 42 to later reproduce that same response state 54 for the user 32. In another embodiment, the user conditions 52 and response state 54 (i.e., feedback) of the user 32 (as well as any other relevant data) can be used to train a user model 40 for the user 32, in an on-line and/or off-line mode.

Temporal based modeling system 38 may utilize any time-based modeling technique, such as a hidden Markoff model (HMM), to implement one or more user models 40 that will drive the specific binaural sounds for an associated user 32. Based on current user conditions 52, response states 54 and/or desired responses of the user 32, the user model 40 will generate a binaural recipe 44 for the user 32. For example, if the user's desired responses were: problem solving, cognitive and calm, as described above in FIG. 3, a user model 40 associated with the user 32 can model the current user conditions 52 and determine what type of binaural recipe 44 is required to achieve those responses for the user 32. Over time, the response state 54 of the user 32 can be factored in as feedback to refine and alter the binaural recipe 44.

In one embodiment, each desired response for a user 32 is mapped to an associated binaural formula. For example, according to a particular user model 40, a problem solving response may be associated with a 38 Hz left-side and 42 Hz right-side pair of gamma waves, cognitive response may be associated with a 15 Hz left-side and 25 Hz right-side pair of beta waves, and a calm response may be associated with a 7 Hz left-side and 10 Hz right-side pair of alpha waves. These desired responses can be further adjusted by the user model 40 based on user conditions 52 and response states 54. In a case such as this where the user 32 selects multiple desired responses, a binaural recipe 44 having combinatorial or additive elements can be created.

Once the binaural recipe 44 is generated, it is fed to a sound synthesis system 46 that manipulates a sound content source 50 to create the prescribed binaural recipe 44 within a sound stream 56. Sound content source 50 can be any type of content, e.g., an internet, broadcast or satellite radio stream, a user playlist, a music storage/playback device, etc. In the case where two or more responses are desired, the binaural sound within the sound stream 56 may be multiplexed over time, e.g., a 10 second time slice for the first binaural formula, 18 second time slice for the second binaural formula, 12 second time slice for the third binaural formula, then repeat. Accordingly, binaural recipe 44 generally includes a set of binaural formulas and in some cases weights associated with each formula. Weights may be used to dictate an importance or efficacy of a particular response, and thus be used to dictate how long each time slice should last.

In an alternative approach, multiple binaural formulas can be overlaid upon each other within the sound stream 56, such that, for example, percussion instruments are used to implement a first formula, string instruments are utilized to implement a second formula, and wind instruments are utilized to implement a third formula.

Once the sound stream is generated, binaural sound output system 48 outputs the sound stream 56 to the user 32, e.g., via a pair of speakers or headphones. In a further embodiment, the sound stream 56 (as well as the binaural recipe 44) may be stored for later use.

As the user 32 is listening, the response state 54 of the user 32 can be fed back into the temporal based modeling system 38 in order to refine the binaural recipe 44 to better achieve the desired response. The feedback can also be used to continue training the user model 40 in an on-line fashion.

Figure 4:
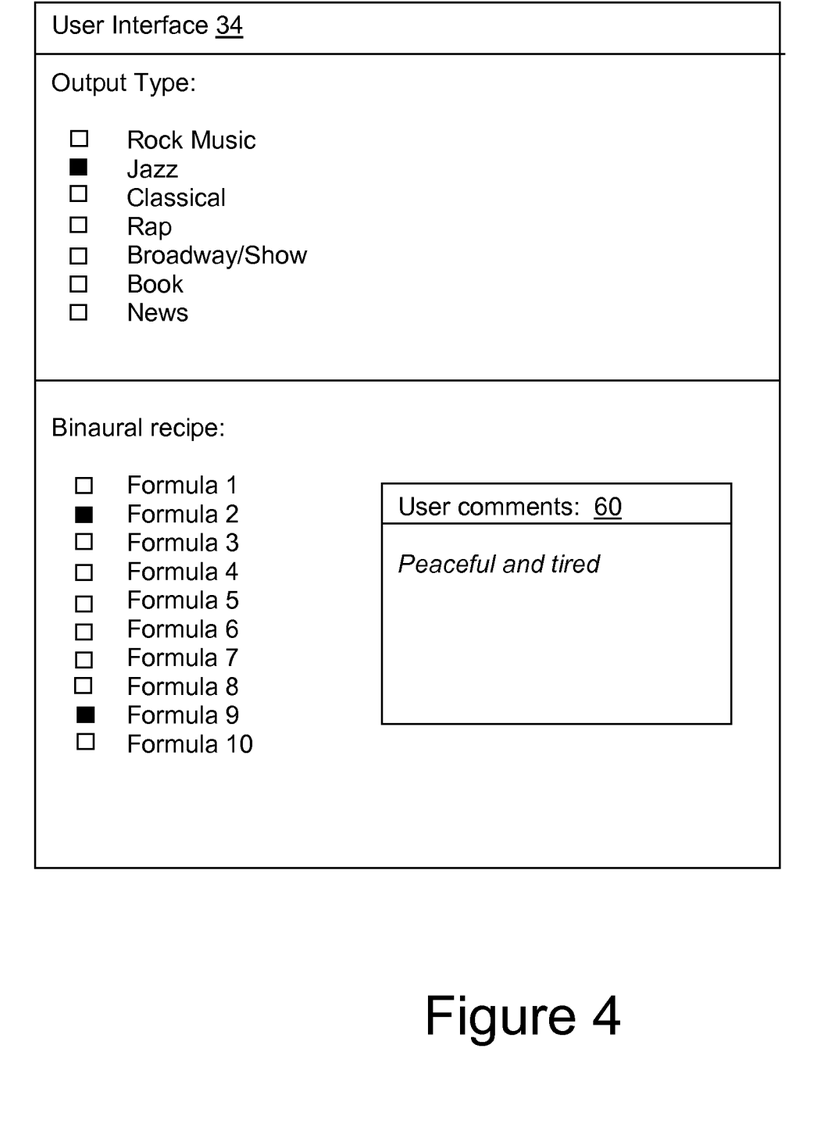
FIG. 4 depicts an illustrative interface for a binaural sound system in accordance with an embodiment of the present invention.

FIG. 4 depicts a further embodiment in which the user 32 (or an automated process) selects a binaural recipe 44 (in this example a combination of formulas 1 and 9) via interface 34. Sound synthesis system 46 then generates a sound stream 56 that is outputted back to the user 32. The user 32 then listens to the sound stream 56 and his or her response 54 is collected, either via monitoring system 36, or via a manual input 60 in the user interface 34. This can be implemented by training system 42 as off-line training or as a mechanism for the user to experiment and achieve a desired response, or both. The user 32 can then create their own menu of responses based on one or more selected formulas.

There exists any number of potential uses of binaural sound system 30. For example, a person who is struggling with depression can utilize system 30 to play audible and/or inaudible sounds to eventually change his or her somatic state. The automatic feedback provided by binaural sound system 30 may be utilized to individualize the binaural sound frequencies based upon depression ratings and physiological human signals. Further, binaural sound is a noninvasive language into the cortical systems (non-human as well). A translation module, e.g., English to Spanish, can be used to provide an interface to move toward English to direct brain entanglement communication. In order for a human to introspect oneself with awareness, human body signatures must communicate state within a human factor. The translation module facilitates such cortical system language to human language.

For mobile devices like smart phones or for gaming systems, applications are available to practice meditation (e.g., yoga and fitness applications). These applications can be extended by the appropriate binaural sounds to support the desired target. For example, based on a measured heart rate variability (HRV) or brainwaves, a binaural sound can be generated to lead the person into the alpha state or even into the theta state. The theta state is slower than alpha with a deeper sense of relaxation, and is known as a highly creative state. The binaural sound can be adjusted as soon the person is in danger drifting into the delta state which is the state of sleep.

Such a binaural feedback concept can also be used to for example support the learning effect while watching a documentary or educational movie. The binaural sounds can be mixed with the music channel and the voice channel. Moreover, the appropriate binaural tone can assist the message of a TV commercial, e.g., for drinking coffee or to stop smoking.

As part of a car assistance system, the interaction of measuring the well-being state of a driver and the generation of the suitable binaural sound can assist the driver by keeping him or her longer focused on the traffic or relaxed in a gentle not disturbing way.

Figure 5:
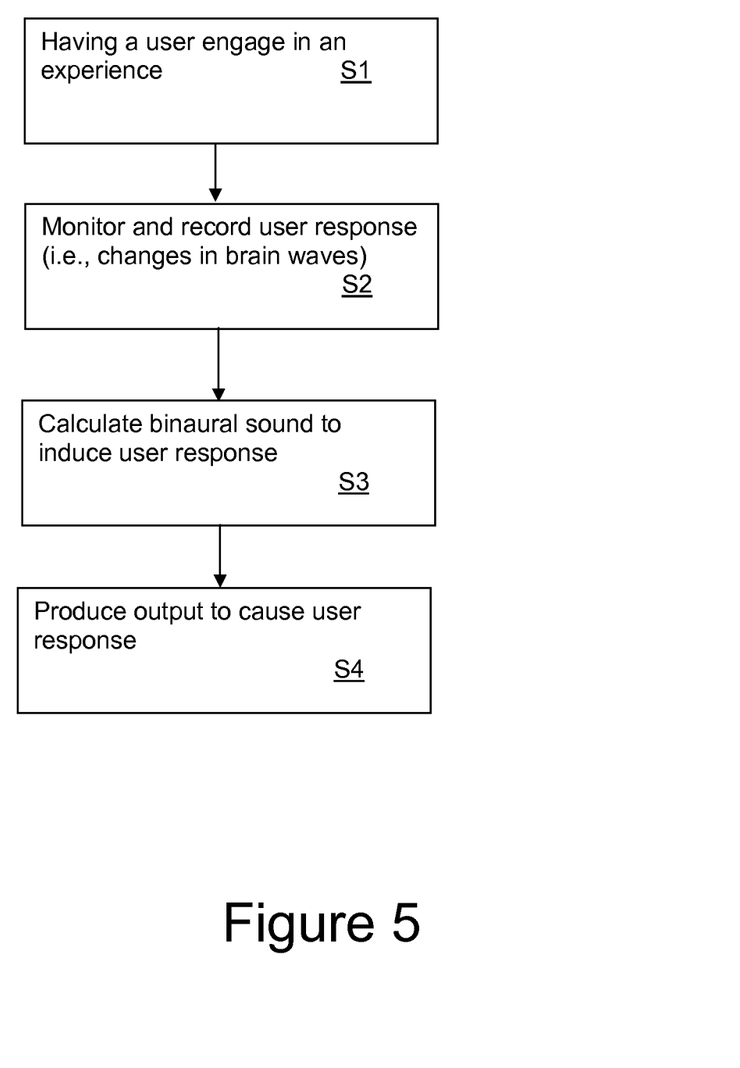
FIG. 5 depicts a flow chart of a method of simulating a user response in accordance with an embodiment of the present invention.

FIG. 5 depicts a flow chart showing a further application of binaural sound using, e.g., binaural sound system 30 (FIG. 2). At S1, the user 32 engages in some physical or mental experience, e.g., meditating, getting married, winning a competition, working out, etc. At S2, changes in the user's brain waves are recorded as a user response by monitoring system 36. At S3, a binaural sound (i.e., a left side signal and a right side signal) are calculated to cause the same response in the user's brain. This may for example be done with temporal based modeling system 38, which for example can examine one or more user models 40 to determine a recipe to achieve the response. At S4, an output (e.g., a sound stream or report) is produced to induce the response within the user 32.

The collection of brain wave data (i.e., user response 54) may be implemented utilizing electroencephalography (EEG), which is the recording of electrical activity along the scalp produced by the firing of neurons within the brain. In the present context, EEG may be utilized to monitor and record the brain's spontaneous electrical activity over a short period of time, e.g., 20-40 minutes, from multiple electrodes placed on the scalp of the user. An event-related potential (ERP) may be measured as part of the user response and generally includes any measured brain response that is directly the result of a thought or perception. A device known as a brain-computer interface (BCI), sometimes called a direct neural interface or a brain-machine interface, may also be utilized to monitor and collect brain wave data. BCI is a direct communication pathway between a brain and an external device. Bas are often aimed at assisting, augmenting or repairing human cognitive or sensory-motor functions.

Note that for the purposes of this disclosure and accompanying claims, the terms "left-side" and "right-side" signals are utilized to simply describe a first signal and a second signal as commonly used in audio terms. The terms are not intended to be limiting in any other manner.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including Instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A binaural sound system, comprising:
an interface for obtaining a plurality of desired responses;
a system for generating a binaural recipe, the binaural recipe comprising a plurality of binaural formulas, each binaural formula for inducing one of the desired responses, each binaural formula having an associated weight indicating an importance of the desired response induced by the binaural formula, wherein the binaural recipe includes left side audio signals and right side audio signals for inducing the plurality of responses;
a sound synthesis system for creating the binaural recipe within a sound stream by time multiplexing the plurality by binaural formulas based on their associated weights; and
an output system for outputting the sound stream containing the left side audio signals and right side audio signals of the binaural recipe.

2. The binaural sound system of claim 1, further comprising a monitoring system for monitoring at least one of: a set of current conditions of a user and a set of user responses.

3. The binaural sound system of claim 2, wherein the system for generating the binaural recipe includes a temporal based modeling system that implements a user model for an associated user.

4. The binaural sound system of claim 3, wherein the temporal based modeling system alters the binaural recipe over time based on the set of user responses monitored by the monitoring system.

5. The binaural sound system of claim 1, wherein the output system comprises a set of headphones.

6. A computer readable medium having a program product stored thereon for processing binaural sounds, comprising:
program code for obtaining a plurality of desired responses;
program code for generating a binaural recipe, the binaural recipe comprising a plurality of binaural formulas, each binaural formula for inducing one of the desired responses, each binaural formula having an associated weight indicating an importance of the desired response induced by the binaural formula, wherein the binaural recipe includes left side audio signals and right side audio signals for inducing the plurality of responses;
program code for creating the binaural recipe within a sound stream by time multiplexing the plurality by binaural formulas based on their associated weights; and
program code for outputting the sound stream containing the left side audio signals and right side audio signals of the binaural recipe.

7. The computer readable medium of claim 6, further comprising program code for monitoring at least one of: a set of current conditions of a user and a set of user responses.

8. The computer readable medium of claim 7, wherein the program code for generating the binaural recipe includes a temporal based modeling system that implements a user model for an associated user.

9. The computer readable medium of claim 8, wherein the temporal based modeling system alters the binaural recipe over time based on the set of user responses being monitored.

* * * * *